United States Patent [19]

Okabe et al.

[11] Patent Number: 5,091,403

[45] Date of Patent: Feb. 25, 1992

[54] SULFINYL IMIDAZOLE DERIVATIVES AND ANTIULCER AGENTS CONTAINING THE SAME

[75] Inventors: Susumu Okabe, Kyoto; Mitsuo Masaki; Tomio Yamakawa, both of Chiba; Hitoshi Matsukura, Saitama; Yutaka Nomura, Chiba, all of Japan

[73] Assignee: Nippon Chemiphar Co., Ltd., Tokyo, Japan

[21] Appl. No.: 565,975

[22] Filed: Aug. 10, 1990

[30] Foreign Application Priority Data

Aug. 10, 1989 [JP] Japan ................................ 1-209192

[51] Int. Cl.⁵ .................... A61K 31/415; C07D 233/84
[52] U.S. Cl. ..................................... 514/398; 548/337
[58] Field of Search ......................... 548/337; 514/398

[56] References Cited

FOREIGN PATENT DOCUMENTS 0251536 1/1988 European Pat. Off. .
301422 2/1989 European Pat. Off. .
0354788 2/1990 European Pat. Off. .

OTHER PUBLICATIONS

Okabe et al., "Preparation and Formulation, Etc." CA 113:97602k (1990).
Honma et al., "Preparation of 1-(Pyridyl or, etc.)" CA 109:211050y (1988).

*Primary Examiner*—Patricia L. Morris
*Attorney, Agent, or Firm*—McAulay Fisher Nissen Goldberg & Kiel

[57] ABSTRACT

Disclosed are novel imidazole derivatives having the formula:

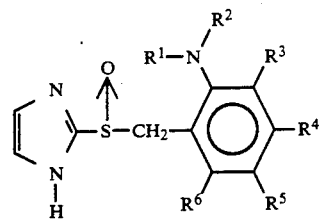

wherein $R^1$ is hydrogen or an alkyl group having 1-6 carbon atoms, $R^2$ is an alkyl group having 2-6 carbon atoms substituted with an alkoxy group having 1-4 carbon atoms, each of $R^3$, $R^4$, $R^5$ and $R^6$ independently is hydrogen, a halogen, an alkyl group having 1-6 carbon atoms, an alkoxy group having 1-6 carbon atoms, a fluorine-substituted alkyl group having 1-6 carbon atoms, or a fluorine-substituted alkoxy group having 1-6 carbon atoms. The new imidazole derivatives are effective particularly as anti-ulcer agents.

6 Claims, No Drawings

SULFINYL IMIDAZOLE DERIVATIVES AND ANTIULCER AGENTS CONTAINING THE SAME

FIELD OF THE INVENTION

The present invention relates to a novel imidazole derivative, particularly an imidazole derivative having the following formula (I):

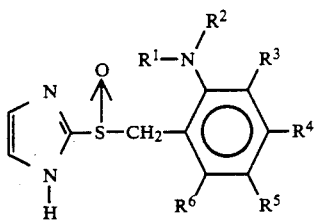

wherein $R^1$ is hydrogen or an alkyl group having 1.6 carbon atoms, $R^2$ is an alkyl group having 2-6 carbon atoms substituted with an alkoxy group having 1-4 carbon atoms, each of $R^3$, $R^4$, $R^5$ and $R^6$ independently is hydrogen, a halogen, an alkyl group having 1.6 carbon atoms, an alkoxy group having 1-6 carbon atoms, a fluorine-substituted alkyl group having 1-6 carbon atoms, or a fluorine substituted alkoxy group having 1-6 carbon atoms.

The invention also relates to a process for the preparation of the imidazole derivative (I) and an anti-ulcer agent containing the imidazole derivative (I) as an effective ingredient.

BACKGROUND OF THE INVENTION

GB 2163747 describes that benzimidazole derivatives having the formula (A):

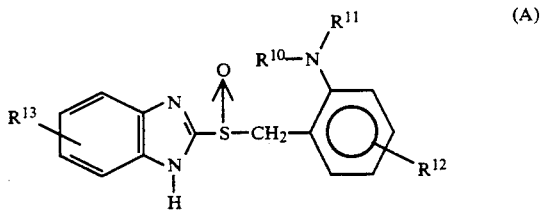

wherein each of $R^{10}$ and $R^{11}$ is hydrogen or a lower alkyl group, and one of $R^{12}$ and $R^{13}$ is a halogen, trifluoro methyl, a lower alkyl group, a lower alkoxy group, a lower alkoxycarbonyl group or amino, are effective as anti-ulcer agents showing $H^+ + K^+$ ATPase inhibitory action.

EP234690A describes that sulfoxides having the formula (B):

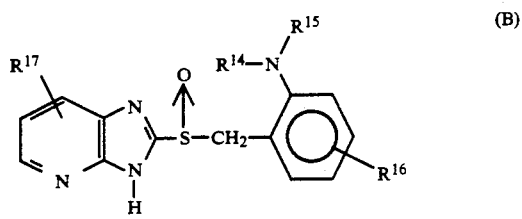

wherein each of $R^{14}$ and $R^5$ is hydrogen or a lower alkyl group and each of $R^{16}$ and $R^{17}$ is hydrogen, a lower alkoxy group or a lower alkyl group, are effective as anti-ulcer agents showing $H^+ + K^+$ ATPase inhibitory action.

SUMMARY OF THE INVENTION

An object of the present invention is to provide a new compound showing a high anti-ulcer action as well as improved safety.

It has been discovered by the present inventors that a novel imidazole derivative having the formula (I) has an excellent gastric juice inhibitory action.

In contrast with the above-mentioned known benzimidazole derivatives and imidazopyridine derivatives, of which imidazole rings are condensed with aromatic rings, the imidazole derivative of the invention does not have an aromatic ring condensed with an imidazole ring. Therefore, the imidazole derivative of the invention structurally is very far from the above-mentioned known compounds.

The imidazole derivative of the invention is effective as anti-ulcer agents and has high safety and improved stability, particularly it has excellent stability in solution.

The present invention provides a novel imidazole derivative (I), which is effective as an anti-ulcer agents.

The invention also provides a new process for the preparation of the imidazole derivative (I).

Further, the invention provides an anti-ulcer agent containing the imidazole derivative (I).

DETAILED DESCRIPTION OF THE INVENTION

The imidazole derivative (I) of the invention can be prepared, for example, by the process which comprises the steps of:

reacting of the compound having the following formula (II):

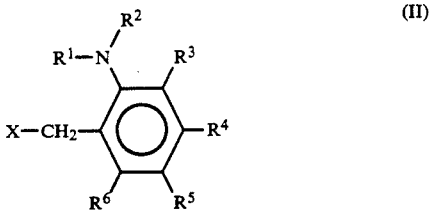

wherein $R^1$ is hydrogen or an alkyl group having 1-6 carbon atoms, $R^2$ is an alkyl group having 2-6 carbon atoms of which one hydrogen is substituted with an alkoxy group having 1-4 carbon atoms, each of $R^3$, $R^4$, $R^5$ and $R^6$ independently is hydrogen, a halogen, an alkyl group having 1-6 carbon atoms of which hydrogen may be substituted with fluorine or an alkoxy group having 1-6 carbon atoms of which hydrogen may be substituted with fluorine and X is a releasable group such as halogen, tosyloxy group or mesyloxy group, with 2-mercaptoimidazole to prepare the imidazole derivative having the formula (III), and oxidizing the imidazole derivative having the formula (III):

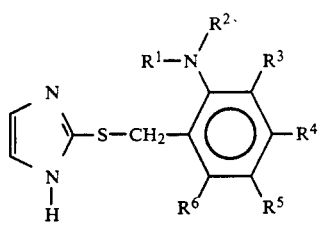

(III)

wherein each of $R^1$, $R^2$, $R^3$, $R^4$, $R^5$ and $R^6$ has the same meaning as defined for the formula (II).

The above reaction between a compound of the formula (II) and 2-mercaptoimidazole can be performed at a temperature from room temperature to the reflux inert solvent such as benzene, ethanol or acetone. The reaction can be carried out in the presence of an alkali agent such as NaOH, KOH, $K_2CO_3$, $NaHCO_3$ and triethylamine for trapping an acid produced in the reaction.

The procedure of the oxidation reaction of the compound of the formula (III) to prepare the sulfinyl-type derivative can be performed in the conventional manner. For instance, a compound of the formula (III) can be oxidized using an oxidizing agent such as aqueous hydrogen peroxide in the presence of a metal ion (e.g., vanadium, molybdenum, or tungsten), and organic peroxide (e.g., m-chloroperbenzoic acid or tert-butylhydroperoxide), or sodium hypochlorite. The reaction can be performed in an inert solvent such as chloroform, dichloromethane, methanol, or ethyl acetate at a temperature in the range of $-30°$ C. to $50°$ C., preferably $15°$ C. to $5°$ C.

In the specification, examples of alkyl group having 1–6 carbon atoms include methyl, ethyl, n-propyl, i-propyl, n-butyl, i-butyl, t-butyl, n-pentyl, i-pentyl, neopentyl, n-hexyl and i-hexyl. Examples of alkoxy group having 1-4 carbon atoms include methoxy, ethoxy, n-propoxy, i-propoxy, n-butoxy, i-butoxy, t-butoxy and cyclopropoxy. Examples of alkyl group having 2-6 carbon atoms include ethyl, n-propyl, i-propyl, n-utyl, i-butyl, t-butyl, n-pentyl, i-pentyl, neopentyl, n-exyl and i-hexyl. With respect to $R^2$ (i-e., an alkyl group having 2-6 carbon atoms substituted with an alkoxy group having 1-4 carbon atoms) in the formula (I), (II) and (III), the alkoxy group having 1-4 carbon atoms is preferably attached to the terminal carbon atom (which is not attached to the nitrogen atom) of the alkyl group having 2-6 carbon atoms. Examples of alkoxy group having 1-6 carbon atoms include methoxy, ethoxy, n-propoxy, i-propoxy, n-butoxy, i-butoxy, t-butoxy, pentyloxy and hexyloxy. With respect to each of $R^3$, $R^4$, $R^5$ and $R^6$ fluorine-substituted alkyl group is fluorine-substituted methyl, fluorine-substituted i-propyl, fluorine-substituted n-butyl, fluorine-substituted i-butyl, fluorine-substituted t-butyl, fluorine-substituted n-pentyl, fluorine-substituted i-pentyl, fluorine-substituted neopentyl, fluorine-substituted n-hexyl, or fluorine-substituted i-hexyl, and fluorine substituted alkoxy group is fluorine-substituted methoxy, fluorine-substituted ethoxy, fluorine-substituted n-propoxy, fluorine-substituted i-propoxy, fluorine-substituted t-butoxy, fluorine-substituted pentyloxy or fluorine-substituted hexyloxy. A halogen atom is fluorine, chlorine, bromine or iodine atom.

Examples of the imidazole derivative of the invention include the following compounds.

Representative examples of the imidazole derivatives represented by the formula (I) are those which have $R^1$, $R^2$, $R^3$, $R^4$, $R^5$ and $R^6$ as defined in Table 1.

TABLE 1

| No. | $R^1$ | $R^2$ | $R^3$ | $R^4$ | $R^5$ | $R^6$ |
|---|---|---|---|---|---|---|
| 1 | H | CH2CH2OMe | H | H | H | H |
| 2 | H | CH2CH2OMe | H | H | Me | H |
| 3 | H | CH2CH2OMe | H | H | H | Me |
| 4 | Me | CH2CH2OMe | H | H | H | H |
| 5 | H | CH2CH2OEt | H | H | H | H |
| 6 | H | (CH2)3OMe | H | H | H | H |
| 7 | H | CH2CH2Oi-Pr | H | H | H | H |
| 8 | H | (CH2)3OEt | H | H | OMe | H |
| 9 | H | (CH2)4OMe | H | OCF3 | H | H |
| 10 | H | CH2CH2OPr | OMe | OMe | H | H |
| 11 | Me | CH2CH2OBu | H | Cl | H | H |
| 12 | H | CH2CH2OEt | H | H | Me | H |
| 13 | H | CH2CH2OMe | H | Me | OMe | Me |
| 14 | H | CH2CH2OEt | H | Me | OMe | Me |
| 15 | H | CH2CH2OMe | H | Cl | OMe | H |
| 16 | H | CH2CH2OMe | H | CF3 | OMe | H |

Remarks:
H: hydrogen, Me: methyl, Et: ethyl, Pr: propyl
i-Pr: isopropyl, Bu: butyl, $CF_3$: trifluoromethyl The pharmacological effects were tested with respect to a representative compound of formula (I) of the invention. The test results are given below.

(1) $H^+ + K^+$ ATPase Inhibitory Effects (Test 1)

Following the method of Forte et al (J. Applied Physiol., 32, 714.717 (1972)), a rabbit gastric mucosa were isolated. A vesicle containing $H^+ + K^+$ ATPase was prepared by centrifuging the cells in Ficoll of discontinuous density gradient according to G. Saccomani et al (Biochim. Biophys. Acta, 465. 311-330 (1977)). After the enzyme was incubated at room temperature for 25 min. in 0.5 ml of a solution which contained 5 mM of an imidazole buffer (pH 6.0) and $2 \times 10^{-4}$ M of 2—[2—(2-methoxyethylamino)benzylsulfinyl] imidazole (the compound of Example 1; the test compound), the mixture was heated to $37°$ C. The mixture was then allowed to stand for further 5 min. To the mixture was added 0.5 ml of a solution which contained 4 mM of magnesium chloride, 80 mM of an imidazole buffer (pH 7.4), 20 mM of potassium chloride and 4 mM of ATP. The resulting mixture was reacted at $37°$ C. for 15 min. and 1 ml of 24 % trichloroacetic acid was then added to terminate the reaction. The inorganic phosphorus liberated was quantitatively determined by the method proposed by Taussky and Shorr (J. Biol. Chem., 202, 675-685 (1953)).

The above procedure was repeated except for not using potassium chloride to determine and ATP are activity in the absence of potassium chloride. The desired $K^+$—dependent ATPase activity was calculated by subtracting the ATPase activity value determined in the absence of KCl from the ATPase activity value determined in the presence of KCl.

As the result of this measurement, the value of $H^+ + K^+$ ATPase inhibitory action of the test compound (the compound of Example 1) was found 73.1 %

(2) $H^+ + K^+$ ATPase Inhibitory Effects (Test 2)

the enzyme was prepared in the same manner described in the above Test 1. After the enzyme was incubated at room temperature for 25 min. in 0.5 ml of a solution which contained 5 mM of an imidazole buffer (pH 6.0 or pH 7.4) and various concentrations of test compound, the mixture was heated to $37°$ C. The mixture was then allowed to stand for further 5 min. The value of $H^+ + K^+$ ATPase inhibitory action of each test compound was determined int he same manner described in the above Test 1.

The results are set forth in Table 2.

TABLE 2

| Tested compound | $H^+ + K^+$ ATPase inhibitory action $IC_{50}$ ($\mu M$) | |
| --- | --- | --- |
| | pH 6.0 | pH 7.4 |
| Example 1 | 43 | 180 |
| Example 2 | 46 | 190 |
| Example 3 | 25 | more than 300 |
| Example 4 | 4.4 | 26 |
| Example 5 | 22 | 53 |
| Example 6 | 13 | 60 |
| Example 7 | 18 | 94 |
| Example 8 | 0.46 | 11 |

(3) Inhibitory action against the secretion of gastric acid (Test I)

Male Donryu rats having a body weight of 200 to 250 g were fasted (while allowing free access to water) for 24 hrs. in accordance with the conventional method [Shay, H. et al, Gastroenterology, 5, 43.61 (1945)]. Under ether anesthesia the pylorus was ligated and 2−[2−(2-methoxyethylamino)benzylsulfinyl] imidazole (the compound of Example 1; the test compound) was administered intraduodenally. Four hours later, each rat was killed and the stomach was removed to collect the gastric juice. The inhibitory action was determined by comparing the acid output which was determined by titration to pH 7.0 with 0.1.N sodium hydroxide by means of an automatic titrator, with the corresponding value of a control rat prepared in the same manner except that a vehicle alone was administered.

As the result of this measurement, the inhibitory action of the test compound (the compound of Example 1) was found 75.9 % and 94.5 % at a dose of 10 mg/kg and 30 mg/kg, respectively.

(4) Inhibitory action against the secretion of gastric acid (Test II)

Heidenhain pouch dogs produced from male beagle dogs were fasted. To the dogs were then administered intra venously histamine hydrochloride (gastric juice secretion inducing agent) continuously at a dose of 160 µg/kg/hr. The gastric juice was collected at an interval of 15 min. to measure the amount of gastric juice and acid output to determine an acid secretion amount (mEq/15 min).

The test compound was intravenously administered to the dogs at one hour after the initiation of histamine ad ministration.

The inhibitory action was determined by comparing the acid secretion amount between pre-drug value (just before drug administration) and post-drug value (30 min. after drug administration).

The results at a dose of 3 mg/kg are set forth in Table 3.

TABLE 3

| Tested compound | Suppressive action (%) |
| --- | --- |
| Example 1 | 89 |
| Example 2 | 97 |
| Example 3 | 85 |
| Example 4 | 89 |

TABLE 3-continued

| Tested compound | Suppressive action (%) |
| --- | --- |
| Example 5 | 98 |
| Example 6 | 92 |

At the other experiment, the test compounds mere administrated orally 2 hours before the initiation of histamine administration, and the inhibitory action was determined by comparing the acid secretion amount wit the corresponding amount of a control dog prepared in the same manner except that a vehicle alone was administered. The results at a dose 10 mn/kg are set forth in Table 4.

TABLE 4

| Tested compound | Suppressive action (%) |
| --- | --- |
| Example 3 | 100 |
| Example 8 | 100 |

Acute toxicity test

Male SD rats having a body weight of about 190 g were orally administered with compound of Example 8. The rats were then observed for 2 days. The MLD was found to be 1,000 mg/kg or more.

The compounds (I) of the present invention can be administrated either orally or parenterally. Preparation forms for oral administration may be, for example, tablets, capsules, powder, granules, syrup and the like. Preparation forms for parenteral administration may be injectable preparations and the like. For the formulation of these preparations, excipients, disintegrants, binders, lubricants, pigments, diluents and the like which are commonly employed in the art may be used. The excipients may include dextrose, lactose and the like. Starch, carboxymethylcellulose calcium and the like may be used as the disintegrants. Magnesium stearate, talc and the like may be used as the lubricants. The binders may be hydroxypropylcellulose, gelatin, polyvinylpyrrolidone and the like.

The dose may usually be about 1 mg/day to 50 mg/day in the case of an injectable preparation and about 10 mg/day to 500 mg/day in the case of oral administration, both for an adult. The dose may be either increased or decreased depending upon the age and other conditions.

Examples of the present invention are given below.

EXAMPLES 1

2- [2-(2-methoxyethylamino)benzylsulfinyl]imidazole (i) methyl 2-methoxyacetamidobenzoate To a solution of 3.02 g (20 mmol) of methyl anthranilate in 30 ml of methylene chloride was added 2.22 g (22 mmol) of triethylamine. Into the mixture, a solution of 2.39 g (22 mmol) of methoxyacetyl chloride in 15 ml of methylene chloride was dropwise added under chilling with ice. The resulting mixture was then stirred for 1 hour. After adding ice, the stirred mixture was made alkaline by addition of 1 N aqueous sodium hydroxide and then extracted with chloroform. The organic portion was collected and washed sequentially with 3 N HCl, 6 N HCl, water and saturated aqueous sodium chloride. The washed chloroform portion was dried over anhydrous sodium sulfate. The solvent was removed by distillation under reduced pressure to obtain 3.6 g of the desired compound.

¹H-NMR (CDCl₃): δ. 3.56 (s, 3H), 3.93 (s, 3H), 4.05 (s, 2H), 6.9-8.8 (m, 4H).

(ii) 2-(2-methoxyethylamino)benzyl alcohol

To a suspension of 912 mg (24 mmol) of lithium aluminium hydride in 40 ml of dry tetrahydrofuran (THF) was dropwise added a solution of 3.6 g (16.1 mmol) of methyl 2-methoxyacetamidobenzoate obtained in the above (i) in 10 ml of dry THF under stirring and chilling with ice for the period of 10 min. The mixture was then stirred for 1 hour. To the reaction mixture, saturated aqueous sodium sulfate was added. The organic portion was collected and placed under reduced pressure to distill off the solvent. The residue was purified by silica gel column chromatography to obtain 1.2 g of the desired compound as a colorless oil.

¹H-NMR (CDCl₃): δ. 3.38 (s, 3H), 3.2-3.4 (m, 2H), 3.5-3.7 (m, 2H), 4.63 (s, 2H), 6.5-7.3 (m, 4H).

(iii) 2-[2-(2-methoxyethylamino)benzylthio]imidazole

To a solution of 1.2 g (6.6 mmol) of 2-(2-methoxyethylamino)benzyl alcohol obtained in the above (ii) in 10 ml of methylene chloride was dropwise added a solution of 0.62 ml (8.6 mmol) of thionyl chloride in 2 ml of methylene chloride under stirring and chilling with ice for the period of 10 min. After the mixture was stirred for 15 min. at room temperature, the solvent was distilled off under reduced pressure. To the obtained residue, 1.32 g (13.2 mmol) of 2-mercaptoimidazole and 10 ml of ethanol was added. The resulting mixture was then stirred for 1.5 hr. at room temperature. The solvent was distilled off under reduced pressure. After adding ice, the residue was made alkaline by addition of 1 N aqueous sodium hydroxide and then extracted with chloroform. The organic portion was collected and washed with water and saturated aqueous sodium chloride. The washed chloroform portion was dried over anhydrous sodium sulfate. The solvent was then removed by distillation under reduced pressure. The residue was purified by silica gel column chromatography to obtain 1.52 g of the desired compound as a colorless oil.

¹H-NMR (CDCl₃): δ. δ=3.44 (s, 3H), 3.2-3.5 (m, 2H), 3.6-3.8 (m, 2H), 4.13 (s, 2H),
6.4-7.2 (m, 4H), 7.00 (s, 2H).

(iv) 2-[2-(2-methoxyethylamino)benzylsulfinyl]imidazole 1.45 g (5.5 mmol) of 2-[2-(2-methoxyethylamino)benzylthio] imidazole obtained in the above (iii) was dissolved in a mixture of 13 ml of methylene chloride, 13 ml of methanol and 1.3 ml of acetic acid. To the resulting mixture were added 2.6 ml of 35 % aqueous hydrogen peroxide and 37 mg of ammonium metavanadate under chilling with ice. Then the obtained mixture was stirred for 2.5 hrs. at the same temperature. After the reaction was completed, a saturated aqueous sodium hydrogencarbonate was added to the stirred mixture. Then the resulting mixture was subjected to ex. traction with chloroform. The organic portion was collected and was further subjected to extraction with 1 N aqueous sodium hydroxide. The aqueous portion was made ammonia-alkaline by addition of 20 % aqueous ammonium chloride. The deposited oily product was extracted with chloroform. The chloroform portion was washed with saturated aqueous sodium chloride and dried over anhydrous sodium sulfate. The solvent was distilled off under reduced pressure and then the residue was crystallized from ether to give 760 mg of the desired compound as a white crystalline powder.

IR ν (KBr): cm⁻¹ 3390, 1605, 1585, 1525, 1475, 1310, 1105, 1000, 885, 745, 505.

¹H-NMR (CDCl₃ / CD₃OD=1/1 v/v): δ. 3.04-3.38 (m, 2H), 3.34 (s, 3H), 3.44-3.70 (m, 2H), 4.26 and 4.56 (each d, 2H, J=14 Hz), 5.08 (m, 1H), 6.4-7.3 (m, 6H)
m.p.: 126-128° C. (decomp.).

EXAMPLE 2

2-[2-(2-isopropoxyethylamino)benzylsulfinyl]imidazole (i) isopropoxyacetic acid 8.4 g of sodium metal was dissolved in 160 ml of isopropyl alcohol under heating. To the resulting solution was added a solution of 20.9 g of bromoacetic acid in 20 ml of isopropyl alcohol at approx. 50° C. for a period of 10 min. The resulting mixture was then heated under reflux for 1 hr. After adding conc. hydrochloric acid, the solvent was distilled off under reduced pressure. To the residue was added ether, and then precipitated inorganic salt was filtered off. The obtained filtrate was dried over anhydrous sodium sulfate. Ether was distilled off and the residue was distilled under reduced pressure to give 5.37 g of the desired compound as a pale yellow oil. (Yield: 30.3 %)

¹H-NMR (CDCl₃): δ. 1.23 (d, 6H, J=6 Hz), 3.73 (m, 1H), 4.12 (s, 2H), 8.79 (bs, 1H). b.p.: 83-87° C. / 5-6 mmHg.

(ii) isopropoxyacetylchloride

A mixture of 5.37 g (46 mmol) of isopropoxyacetic acid and 3.7 ml of thionyl chloride was stirred over night at room temperature, then heated and further stirred for 1.5 hr. at 55° C. The resultant solution was distilled under reduced pressure to obtain 4.43 g of the desired compound as a colorless oil. (Yield: 71.3 %)

¹H-NMR (CDCl₃): δ. 1.21 (d, 6H, J=6 Hz), 3.72 (m, 1H), 4.40 (s, 2H). b.p.: 70° C. / 77 mmHg.

(iii) methyl (2-isopropoxyacetamido)benzoate

To a solution of 4.90 g (33 mmol) of methyl anthranilate and 6.1 ml of triethylamine in 50 ml of dichloromethane was dropwise added a solution of 4.43 g (33 mmol) of isopropoxyacetylchloride in 20 ml of dichloromethane under chilling with ice for a period of 15 min. The resulting mixture was stirred over night at room temperature. The reaction mixture was washed sequentially with 5 % aqueous sodium carbonate, 3 N hydrochloric acid and 5% aqueous sodium carbonate, and then was dried over anhydrous sodium sulfate. The solvent was distilled off to leave 5.59 g of the desired compound as a residual pale brown oil. (Yield: 68.6 %)

¹H-NMR (CDCl₃): δ. 1.20 (d, 6H, J=6 Hz), 3.74 (m, 2H), 3.92 (s, 3H), 4.09 (s, 2H), 6.9.8.8 (m, 4H) 11.74 (bs, 1H).

(iv) 2-(2-isopropoxyethylamino)benzyl alcohol

To a suspension of 2.12 g of lithium aluminium hydride in 50 ml of THF was dropwise added a solution of 5.59 g of methyl (2.isopropoxyacetamido)benzoate in 20 ml of THF under chilling with ice for a period of 15 min. The mixture was then heated under reflux for 1 hr. To the resulting mixture, a saturated aqueous sodium sulfate was added under chilling with ice to decompose the excess lithium aluminium hydride. The organic portion was collected and the solvent was removed. The residue was dissolved in chloroform. The resulting solution was washed with water and dried over hydrous sodium sulfate. Chloroform was distilled off to leave 5.19 g of the desired compound (purity: 89.7 %) as a pale brown oil.

$^1$H-NMR (CDCl$_3$): δ. 1.17 (d, 6H, J=6 Hz), 3.28 (t, 2H, J=5 Hz), 3.3–3.8 (m, 3H), 4.63 (s, 2H), 6.4–7.3 (m, 4H)

(v) 2-[2-(2-isopropoxyethylamino)benzylthio]imidazole

To a solution of 5.19 g (22 mmol) of 2-(2-isopropoxyethylamino)benzyl alcohol obtained in the above (iv) in 50 ml of dichloromethane was dropwise added a solution of 2.4 ml of thionyl chloride in 10 ml of dichloromethane under chilling with ice for a period of 10 min. The resulting mixture was stirred for 30 min. The solvent was distilled off to obtain a pale yellow crystalline product. The crystalline product was added to a solution of 2-66 g of 2.mercaptoimidazole in 27 ml of ethanol for 15 min. and then the mixture was stirred for 30 min. at room temperature. Ethanol was distilled off. To the residue were added chloroform and 5 % aqueous sodium carbonate. The organic portion was collected and dried over anhydrous sodium sulfate. Chloroform was distilled off. The residue was purified by silica gel column chromatography and crystallized from ether/hexane to give 2.40 g of the desired compound as a white crystalline powder. (Yield: 37.0 %)

$^1$H-NMR (CDCl$_3$): δ. 1.20 (t, 6H, J=6 Hz), 3.34 (t, 2H, J=5 Hz), 3.4–3.9 (m, 3H), 4.12 (s, 2H), 6.3–7.3 (m, 4H), 6.98 (s, 2H).

(vi) 2-[2-(2-isopropoxyethylamino)benzylsulfinyl]imidazole 1.50 g (5.2 mmol) of 2-[2-(2-isopropoxyethylamino)benzylthio]imidazole was dissolved in a mixture of 15 ml of dichloromethane, 15 ml of methanol and 1.5 ml of acetic acid. To the resulting mixture were added 2.3 ml of 35 % aqueous hydrogen peroxide and 48 mg of ammonium metavanadate under chilling with ice. Then the mixture was stirred for 2 hrs. under chilling with ice. After the reaction was completed, 5 % aqueous sodium carbonate was added to the stirred mixture. The organic portion was collected and was subjected to extraction with 20 ml of 0.2 N aqueous sodium hydroxide. To the collected aqueous portion was little by little added 60 ml of 1 N aqueous ammonium chloride. The deposited oily product was extracted with chloroform. The chloroform extractant was dried over anhydrous sodium sulfate and then chloroform was distilled off. The residue was crystallized from ether to give 1.20 g of the desired compound as a white crystalline powder. (Yield: 75.8 %)

IR ν (KBr): cm$^{-1}$. 3360, 2970, 2950, 2850, 1600, 1580, 1520, 1460, 1320, 1310, 1265, 1150, 1130, 1100, 1080, 1035, 750, 500.

$^1$H-NMR (CDCl$_3$ / CD$_3$OD=1/1 v/v): δ. 1.21 (d, 6H, J=6 Hz), 3.26 (t, 2H, J=5 Hz), 3.5–3.8 (m, 3H), 4.31 (d, 1H, J=14 Hz), 4.54 (d, 1H, J=14 Hz), 6.4–7.3 (m, 4H), 7.21 (s, 2H).

m.p.: 140–142° C. (decomp.).

EXAMPLE 3

2-[2-(2-methoxyethylamino) 5-methylbenzylsulfinyl]imidazole (i) methyl (2-methoxyacetamido-5-methyl)benzoate In a solution of 4.00 g (24 mmol) of methyl 5-methylanthranilate and 5.2 ml of triethylamine in 40 ml of dichloromethane was dropwise added a solution of 3.42 g (32 mmol) of methoxyacetylchloride in 10 ml of dichloromethane under chilling with ice for a period of 15 min. The resulting mixture was stirred over night at room temperature. The reaction mixture was washed sequentially with 5 % aqueous sodium carbonate, 3 N hydrochloric acid and 5% aqueous sodium carbonate, and then dried over anhydrous sodium sulfate. The solvent was distilled off to give 5.50 g of the desired compound as a pale brown crystal. (Yield: 95.7 %)

$^1$H-NMR (CDCl$_3$): δ. 2.33 (s, 3H), 3.56 (s, 3H), 3.93 (s, 3H), 4.05 (s, 2H), 7,1–8.7 (m, 3H).

(ii) 2 (2-methoxyethylamino)-5-methylbenzyl alcohol

To a suspension of 1.76 g of lithium aluminium hydride in 55 ml of THF was dropwise added a solution of 5.50 g (23 mmol) of methyl (2.methoxyacetamido.5.methyl)benzoate in 20 ml of THF under chilling with ice for a period of 15 min. The mixture was then heated under reflux for 1 hr. To the resulting mixture, a saturated aqueous sodium sulfate was added under chilling with ice to decompose the excess lithium aluminium hydride. The organic portion was collected and the solvent was removed. The residue was dissolved in chloroform. The resulting solution was washed with water and dried over anhydrous sodium sulfate. Chloroform was distilled off to leave 4.88 g of the desired compound (purity: 92.7 %) as a residual pale brown oil.

$^1$H-NMR (CDCl$_3$): δ. 2.23 (s, 3H), 3.1–3.7 (m, 4H), 3.37 (s, 3H) 4.60 (s, 2H), 6.4–7.1 (m, 3H)

(iii) 2-[2- (2-methoxyethylamino) 5-methylbenzylthio]imidazole

To a solution of 4.88 g (23 mmol) of 2-(2-methoxyethylamino)-5-methylbenzyl alcohol obtained in the above (ii) in 50 ml of dichloromethane was dropwise added a solution of 2.5 ml of thionyl chloride in 10 ml of dichloromethane under chilling with ice for a period of 15 min. The resulting mixture was stirred for 30 min. at room temperature. The solvent was distilled off to leave a residual oily product. The oily product was dissolved in 15 ml of dichloromethane. The dichloromethane solution was added to a solution of 2.78 g of 2.mercaptoimidazole in 30 ml of ethanol for 15 min. and then the mixture was stirred for 30 min. at room temperature. Ethanol was distilled off. To the residue were added chloroform and 5 % aqueous sodium carbonate. The organic portion was collected and dried over anhydrous sodium sulfate. Chloroform was distilled off. The residue was purified by silica gel column chromatography and crystallized from ether/hexane to give 4.91 g of the desired compound as a pale brown crystalline powder. (Yield: 76.4 %)

$^1$H-NMR (CDCl$_3$): δ. δ=2.15 (s, 3H), 3.35 (t, 2H, J=5 Hz), 3.43 (s, 3H), 3.72 (t, 2H, J =5 Hz), 4.11 (s, 2H), 6.4–7.0 (m, 3H), 7.01 (s, 2H).

(iv) 2-[2-(2-methoxyethylamino)-5-methylbenzylsulfinyl]imidazole 1.50 g (5.4 mmol) of 2-[2-(2- methoxyethylamino) 5. o methylbenzylthio]imidazole was dissolved in a mixture of 15 ml of dichloromethane, 15 ml of methanol and 1.5 ml of acetic acid. To the resulting mixture were added 2.3 ml of 35 % aqueous hydrogen peroxide and 46 mg of ammonium metavanadate under chilling with ice. Then the obtained mix ture was stirred for 2 hrs. under chilling with ice. After the reaction was completed, 5 % aqueous sodium carbonate was added to the stirred mixture. The organic portion was collected and washed with 20 ml of 0.05 N aqueous sodium hydroxide, then subjected to extraction with 10 ml of 1 N aqueous sodium hydroxide. In the collected aqueous portion was little by little added 40 ml of 1 N aqueous ammonium chloride. The deposited crystalline product was collected by filtration and washed with sufficient ether and water to give 1.04 g of the desired compound as a pale brown crystalline powder. (Yield: 65.5 %)

IR ν (KBr): cm$^{-1}$. 3320, 2990, 2910, 2850, 2810, 1600, 1525, 1475, 1440, 1420, 1310, 1125, 1110, 1020, 970, 795, 785.

$^1$H-NMR (CDCl$_3$ / CD$_3$OD=1/1 v/v)): δ. 2.14 (s, 3H), 3.24 (t, 2H, J=5 Hz), 3.42 (s, 3H), 3.64 (t, 2H, J=5 Hz), 4.30 (d, 1H, J=13 Hz), 4.50 (d, 1H, J=13 Hz), 6.4–7.1 (m, 3H), 7.23 (s, 2H). m.p.: 147–149° C. (decomp.) 2-[2-(2-methoxyethylamino)-6-methylbenzylsulfinyl]imidazole (i) methyl (2-methoxyacetamido-6-methyl)benzoate In a solution of 5.00 g (30 mmol) of methyl (2-amino-6-methyl)benzoate and 5.0 g of triethylamine in 50 m dichloromethane was dropwise added a solution of 4.67 g (43 mmol) of methoxyacetylchloride in 10 ml of dichloromethane under chilling with ice for a period of 15 min. The resulting mixture was stirred for 30 min. at room temperature. The stirred mixture was washed sequentially with water, 3 N hydrochloric acid and water, and then was dried over anhydrous sodium sulfate. Chloroform was distilled off to leave 7.67 g of the desired compound as a residual pale brown oil. (Purity: 93.6 %)

$^1$H-NMR (CDCl$_3$): δδ=2.44 (s, 3H), 3.52 (s, 3H), 3.94 (s, 3H), 4.00 (s, 2H), 6.8.7.3 (m, 3H).

(ii) 2-(2-methoxyethylamino) 6-methylbenzyl alcohol

To a suspension of 2.28 g of lithium aluminium hydride in 45 ml of dry ether was dropwise added a solution of 7.76 g (30 mmol) of methyl (2.methoxyacetoamido-6-methyl)benzoate obtained in the above (i) in 20 ml of dry ether under chilling with ice for a period of 20 min. The mixture was then heated under reflux for 1 hr. To the resulting mixture, a saturated aqueous sodium sulfate was added under chilling with ice to decompose the excess lithium aluminium hydride. The organic portion was collected and dried over anhydrous sodium sulfate. The solvent was distilled off to leave 5.42 g of the desired compound as a residual pale brown crystal. (Yield: 91.7 %)

$^1$H-NMR (CDCl$_3$): δ. 2.31 (s, 3H), 3.27 (t, 2H, J=5 Hz) 3.36 (s, 3H), 3.60 (t, 2H, J=5 Hz) 4.69 (s, 2H), 6.3–7.2 (m, 3H).

(iii) 2-[2-(2-methoxyethylamino-6-methyl)benzylthio]imidazole

To a solution of 5.42 g (28 mmol) of 2 (2-methoxyethylamino)-6-methylbenzyl alcohol in 55 ml of dichloromethane was dropwise added a solution of 2.7 ml of thionyl chloride in 10 ml of dichloromethane under chilling with ice for a period of 10 min. The resulting mixture was stirred for 30 min. under chilling with ice. The solvent was distilled off to obtain a pale yellow crystalline product. The crystalline product was added to a solution of 3.36 g of 2.mercaptoimidazole in 35 ml of ethanol for 15 min. and then the obtained mixture was stirred for 30 min. at room temperature. Ethanol was distilled off. To the residue were added chloroform and 5 % aqueous sodium carbonate. The organic portion was collected and dried over anhydrous sodium sulfate. Chloroform was distilled off. The residue was purified by silica gel column chromatography and crystallized from ether/hexane to give 5.27 g of the desired compound as a white crystal. (Yield: 68.4 %)

$^1$H-NMR (CDCl$_3$): δ. 2.21 (s, 3H), 3.32 (t, 2H, J=5 Hz), 3.42 (s, 3H), 3.71 (t, 2H, J=5 Hz), 4.20 (s, 2H), 6.3–7.1 (m, 3H), 7.03 (s, 2H).

(iv) 2-[2-(2-methoxyethylamino) 6-methylbenzylsulfinyl]imidazole 1.50 g (5.4 mmol) of 2-[2-(2-methoxyethylamino)-6-methylbenzylthio]imidazole was dissolved in a mixture ml of chloroform, 15 ml of methanol and 1.5 ml of acetic acid. To the resulting mixture were added 2.3 ml of 35 % aqueous hydrogen peroxide and 48 mg of ammonium metavanadate under chilling with ice. Then the obtained mixture was stirred for 1.5 hr. under chilling with ice. After the reaction was completed, 5 % aqueous sodium carbonate was added to the stirred mixture. The organic portion was collected and washed with 20 ml of 0.05 N aqueous sodium hydroxide, then subjected to extraction with 20 ml of 0.5 N aqueous sodium hydroxide. To the collected aqueous portion was little by little added 15 ml of 1 N aqueous ammonium chloride. The deposited oily product was extracted with chloroform. The chloroform extractant was dried over anhydrous sodium sulfate and then chloroform was distilled off. The residue was crystallized from ether to give 1.09 g of the desired compound as a white crystalline powder. (Yield: 68.7 %)

IR ν (KBr): cm$^{-1}$. 3340, 2870, 1585, 1520, 1470, 1440, 1305, 1105, 1020, 960, 770

$^1$H-NMR (CDCl$_3$ / CD$_3$OD=2/1 v/v): δ. 2.22 (s, 3H), 3.1–3.8 (m, 4H), 3.42 (s, 3H), 4.39 (d, 1H, J=14 Hz), 4.62 (d, 1H, J=14 Hz), 6.4–7.2 (m, 3H), 7.27 (s, 2H). m.p.: 129–132° C. (decomp.).

EXAMPLE 5

2-[2-(2-ethoxyethylamino)benzylsulfinyl]imidazole (i) methyl (2-ethoxyacetamido)benzoate To a solution of 4.53 g (30 mmol) of methyl anthranilate and 6.1 ml of triethylamine in 50 ml of dichloromethane was dropwise added a solution of 4.41 g (36 mmol) of ethoxyacetylchloride in 10 ml of dichloromethane under chilling with ice for a period of 15 min. The resulting mixture was stirred for 1 hr. at room temperature. The stirred mixture was washed sequentially with water, 4 N hydrochloric acid and 5% aqueous sodium carbonate, and then was dried over anhydrous sodium sulfate. The solvent was distilled off to leave 7.66 g of the desired compound (purity: 92.8 %) as a residual pale brown oil.

$^1$H-NMR (CDCl$_3$): δ. 1.37 (t, 3H, J=7 Hz), 3.70 (q, 2H, J=7 Hz), 3.93 (s, 3H), 4.10 (s, 2H), 6.9–8.8 (m, 4H).

(ii) 2-(2-ethoxyethylamino)benzyl alcohol

To a suspension of 3.42 g of lithium aluminium hydride in 90 ml of THF was dropwise added a solution of 7.66 g (30 mmol) of methyl (2.ethoxyacetamido)benzoate obtained in the above (i) in 15 ml of THF under chilling with ice for a period of 10 min. The mixture was then heated under reflux for 1 hr. at 70° C. To the resulting mixture, a saturated aqueous sodium sulfate was added under chilling with ice to decompose the excess lithium aluminium hydride. The organic portion was collected and the solvent was removed. The residue was dissolved in chloroform. The resulting solution was washed with water and dried over anhydrous sodium sulfate. Chloroform was distilled off to leave 5.27 g of the desired compound as a colorless oil. (Yield: 90.1 %)

$^1$H-NMR (CDCl$_3$): δ. 1.20 (t, 3H, J=7 Hz), 3.30 (t, 2H, J=5 Hz), 3.53 (q, 2H, J=7 Hz), 3.66 (t, 2H, J=5 Hz), 4.62 (s, 2H), 6.4–7.4 (m, 4H).

(iii) 2-[2-(2-ethoxyethylamino)benzylthio]imidazole

In a solution of 5.27 g (27 mmol) of 2 (2.ethoxyethylamino)benzyl alcohol in 50 ml of dichloromethane was drop wise added a solution of 3.0 ml of thionyl chloride in 10 ml of dichloromethane under chilling with ice for a period of 10 min. The resulting mixture was stirred for 30 min. under chilling with ice. The solvent was distilled off to obtain a pale yellow crystalline product. The crystalline product was added to a solution of 3.24 g of 2.mercaptoimidazole in 35 ml of ethanol for a period of 15 min. and then the mixture was stirred for 30 min. at room temperature. Ethanol was distilled off. To the residue were added chloroform and 5 % aqueous sodium carbonate. The organic portion was collected and dried over anhydrous sodium sulfate. Chloroform was distilled off. The residue was purified by silica gel column chromatography and crystallized from ether/hexane to give 3.25 g of the desired compound as a pale yellow crystal. (Yield: 43.4 %)

$^1$H-NMR (CDCl$_3$): δ. 1.22 (t, 3H, J=7 Hz), 3.37 (t, 2H, J=5 Hz), 3.61 (q, 2H, J=7 Hz), 3.78 (t, 2H, J=5 Hz), 4.13 (s, 2H), 6.4.7.3 (m, 4H).
6.99 (s, 2H).

(iv) 2-[2-(2-ethoxyethylamino)benzylsulfinyl]imidazole
1.50 g (5.4 mmol) of 2-[2-(2-ethoxyethylamino)benzyl thio]imidazole was dissolved in a mixture of 15 ml of chloroform, 15 ml of methanol and 1.5 ml of acetic acid. To the resulting mixture were added 2.3 ml of 35 % aqueous hydrogen peroxide and 48 mg of ammonium metavanadate under chilling with ice. Then the obtained mixture was stirred for 3 hrs. under chilling with ice. After the reaction was completed, 5 % aqueous sodium carbonate was added to the stirred mixture. The organic portion was collected and washed with 0.1 N aqueous sodium hydroxide, then subjected to extraction with 20 ml of 1 N aqueous sodium hydroxide.
In the collected aqueous portion was little by little added ml of 1 N aqueous ammonium chloride. The deposited oily product was extracted with chloroform. The chloroform extractant was dried over anhydrous sodium sulfate and then chloroform was distilled off. The residue was crystallized from ether to give 0.84 g of the desired compound as a white crystalline powder. (Yield: 52.9 %)

IR ν (KBr): cm$^{-1}$. 3370, 2870, 2840, 1605, 1585, 1525, 1310, 1130 1115, 1110, 1040, 750, 500.

$^1$H-NMR (CDCl$_3$ / CD$_3$OD=1/1 v/v): δ. 1.24 (t, 3H, J=7 Hz), 3.28 (t, 2H, J=5 Hz), 3.59 (q, 2H, J=7 Hz), 3.69 (t, 2H, J=5 Hz), 4.31 (d, 1H, J=13 Hz), 4.53 (d, 1H, J=13 Hz), 6.4.7.3 (m, 4H) 7.21 (s, 2H) m.p.: 119-121° C. (decomp.).

EXAMPLE 6

2-[2-(3-methoxypropylamino)benzylsulfinyl]imidazole (i) 3-methoxypropionic acid sodium salt To a solution of 25 g (212 mmol) of methyl 3.methoxypropionate in 250 ml of methanol was dropwise added a solution of 8.9 g (212 mmol) of sodium hydroxide in 25 ml of water under chilling with ice.. The mixture was stirred for 30 min. at the same temperature, and then placed in a refrigerator over night. The solvent was distilled off under reduced pressure. The residue was dried under reduced pressure to obtain 26.2 g of the desired compound. (Yield: 98.1 %)

$^1$H-NMR (CD$_3$OD):δ. 2.41 (t, 2H, J=7 Hz), 3.33 (s, 3H), 3.63 (q, 2H, J=7 Hz).

(ii) methyl N-(3-methoxypropanoyl)anthranilate

To a suspension of 12.6 g (100 mmol) of the sodium salt obtained in the above (i) in 100 ml of benzene was dropwise added 8.0 ml (110 mmol) of thionyl chloride under stirring at room temperature for a period of 5 min. The mixture was then heated under reflux for 30 min. After chilling with ice, insolubles were removed by filtration. To the filtrate were added 15.1 g (100 mmol) of methyl anthranilate and 13.8 g (100 mmol) of potassium carbonate. The resulting mixture was then heated under reflux for 4 hrs. After the addition of ice water, the reaction mixture was washed sequentially with 6 N hydrochloric acid, saturated aqueous sodium hydrogencarbonate and saturated aqueous sodium chloride, and then was dried over anhydrous sodium sulfate. The solvent was distilled off to leave 8.8 g of an oily product. The oily product was crystallized from hexane to give 8.3 g of the desired compound as a pale yellow crystal.

$^1$H-NMR (CDCl$_3$): δ. 2.69 (t, 2H, J=6 Hz), 3.40 (s, 3H), 3.76 (t, 2H, J=6 Hz), 3.91 (s, 3H), 7.05 (dt, 1H, J=1 Hz, 8 Hz), 7.52 (dt, 1H, J=2 Hz, 8 Hz), 8.00 (dd, 1H, J=2 Hz, 8 Hz), 8.73 (dd, 1H, J=1 Hz, 8 Hz), (iii) 2-(3-methoxypropyl)aminobenzyl alcohol To a suspension of 0.96 g (25.3 mmol) of lithium aluminium hydride in 40 ml of dry THF was dropwise added a solution of 4.0 g (16.9 mmol) of methyl N.(3.methoxypropanoyl) anthranilate in 10 ml of dry THF under chilling with ice for a period of 15 min. The mixture was then heated under reflux for 1 hr. To the resulting mixture, a saturated aqueous sodium sulfate was added under chilling with ice to decompose the excess lithium aluminium hydride. After the addition of 40 ml of ether, insolubles were removed by sellaite filtration. The organic portion was collected and dried over anhydrous sodium sulfate, then the solvent was distilled off under reduced pressure to leave 3.1 g of the desired compound as a pale yellow oil. (Yield: 94.0 %)

$^1$H-NMR (CDCl$_3$): δ. 1.92 (m, 2H), 3.25 (t, 2H, J=6 Hz), 3.34 (s, 3H), 3.51 (t, 2H, J=6 Hz), 4.62 (s, 2H), 6.4–7.5 (m, 4H).

(iv) 2-[2-(3-methoxypropylamino)benzylthio]imidazole

To a solution of 2.9 g (14.8 mmol) of 2-(3-methoxypropyl) aminobenzyl alcohol in 29 ml of dichloromethane was dropwise added a solution of 1.3 ml (17.8 mmol) of thionyl chloride in 3 ml of dichloromethane under chilling with ice for a period of 5 min. The resulting mixture was stirred for 15 min. at room temperature. The solvent was distilled off under reduced pressure at room temperature. To the residue was added 10 ml of dichloromethane. The obtained dichloromethane solution was little by little added to a solution of 2.22 g (22.2 mmol) of 2.mercaptoimidazole in 22 ml of ethanol, and then the mixture was stirred for 15 min. at room temperature. Ethanol was distilled off under reduced pressure. To the residue were added ice and saturated aqueous sodium hydrogencarbonate. The resulting mixture was treated with ether for extraction. The organic portion was collected and sequentially washed with saturated aqueous sodium hydrogencarbonate and saturated aqueous sodium chloride, then dried over anhydrous sodium sulfate. The solvent was distilled off under reduced pressure. The residue was purified by silica gel column chromatography to give 2.7 g of the desired compound as a pale yellow oil. (Yield: 65.8 %)

$^1$H-NMR (CDCl$_3$): δ. 1.92 (m, 2H), 3.23 (t, 2H, J=6 Hz), 3.32 (s, 3H), 3.54 (t, 2H, J=6 Hz), 4.14 (s, 2H), 6.3-7.2 (m, 4H), 7.02 (s, 2H)

(v) 2-[2-(3-methoxypropylamino)benzylsulfinyl]imidazole

To a solution of 2.7 g (9.74 mmol) of 2-[2-(3-methoxy. propylamino)benzylthio]imidazole in 27 ml of chloroform was added 2.1 g (purity: 80 %, 9.74 mmol) of m-chloroperbenzoic acid under chilling with ice for a period of about. 10 min. After the reaction was completed, saturated aqueous sodium hydrogencarbonate was added. The resulting mixture was treated with 30 ml of chloroform for extraction. The chloroform portion was collected and washed sequentially with saturated aqueous sodium hydrogencarbonate and 6 ml of 1 N aqueous sodium hydroxide. The washed solution was treated with 6 ml of 1 N aqueous sodium hydroxide (6 mmol) for extraction. The alkaline portion was made ammonia-alkaline by addition of saturated ammonium chloride, and then extracted with chloroform. The organic portion was collected and washed with saturated aqueous sodium chloride, then dried over anhydrous sodium sulfate. The solvent was distilled off under reduced pressure. The residue was crystallized from acetonitrile/ether to obtain 890 mg of the desired compound as a yellow crystal. (Yield: 31.2 %)

IR ν (KBr): cm$^{-1}$. 3390, 2870, 1600, 1580, 1510, 1310, 1115, 1100 1035, 1000, 890, 745.

$^1$H-NMR (CDCl$_3$): δ. 1.86 (m, 2H), 2.9.3.2 (m, 2H), 3.32 (s, 3H), 3.49 (t, 2H, J=6 Hz), 4.23, 4.52 (each d, 2H, J=13 Hz), 4.95 (br, 1H), 6.4.7.3 (m, 6H), m.p.: 100-107° C. (decomp.).

EXAMPLE 7

2-[2-(2-ethoxyethylamino) 5-methylbenzylsulfinyl]imidazole (i) methyl (2-ethoxyacetamido-5-methyl)benzoate To a solution of 4.95 g (30 mmol) of methyl 5-methylanthranilate and 6.5 ml of triethylamine in 50 ml of dichloromethane was dropwise added a solution of 4.78 g (39 mmol) of ethoxyacetylchloride in 15 ml of dichloromethane under chilling with ice for a period of 15 min. The resulting mixture was stirred over night at room temperature. The reaction mixture was washed sequentially with 5 % aqueous sodium carbonate, 3 N hydrochloric acid and 5% aqueous sodium carbonate, and then dried over anhydrous sodium sulfate. Dichloromethane was distilled off to leave 7.60 g of the desired compound (Purity: 99.1 %) as a residual pale brown crystal.(Yield: theoretical)

$^1$H-NMR (CDCl$_3$): δ. 1.37 (t, 3H, J=7 Hz), 2.33 (s, 3H), 3.69 (q, 2H, J=7 Hz), 3.92 (s, 3H), 4.09 (s, 2H), 7.1.8.7 (m, 3H).

(ii) 2-(2-ethoxyethylamino)-5-methylbenzyl alcohol

To a suspension of 2.28 g of lithium aluminium hydride in 70 ml of THF was dropwise added a solution of 7.60 g (30 mmol) of methyl (2.ethoxyacetamido.5 methyl)benzoate in 20 ml of THF under chilling with ice for a period of 15 min. The mixture was then heated under reflux for 1 hr. To the resulting mixture, a saturated aqueous sodium sulfate was added under chilling with ice in order to decompose the excess lithium aluminium hydride. The organic portion was collected by decantation and the solvent was removed. The residue was dissolved in chloroform. The resulting solution was washed with water and dried over anhydrous sodium sulfate. Chloroform was distilled off to leave 7.19 g of the desired compound (purity: 87.2 %) as a residual pale brown oil. (Yield: theoretical)

$^1$H-NMR (CDCl$_3$): δ. 1.20 (t, 3H, J=7 Hz), 2.23 (s, 3H), 3.28 (t, 2H, J=6 Hz), 3.52 (q, 2H, J=7 Hz), 3.64 (t, 2H, J=6 Hz), 4.60 (s, 2H), 6.4.7.1 (m, 3H).

(iii) 2-[2-(2-ethoxyethylamino) 5-methylbenzylthio] imidazole

In a solution of 7.19 g (30 mmol) of 2.(2.ethoxyethylamino) -5-methylbenzyl alcohol obtained in the above (ii) in 60 ml of dichloromethane was dropwise added a solution of 2.8 ml of thionyl chloride in 10 ml of dichloromethane under chilling with ice for a period of 15 min. The resulting mixture was stirred for 30 min. at room temperature. The solvent was distilled off to leave a residual brown oily product. The oily product was dissolved in 20 ml of dichloromethane. The dichloromethane solution was added to a solution of 3.60 g of 2.mercaptoimidazole in 36 ml of ethanol for a period of 15 min. and then the mixture was stirred for 30 min. at room temperature. Ethanol was distilled off. To the residue were added chloroform and 5 % aqueous sodium carbonate. The organic portion was collected and dried over anhydrous sodium sulfate. Chloroform was distilled off. The residue was crystallized from ether/-hexane to give 6.82 g of the desired compound as a pale brown crystalline powder. (Yield: 78.1 %)

$^1$H-NMR (CDCl$_3$): δ. 1.23 (t, 3H, J=7 Hz), 2.15 (s, 3H), 3.35 (t, 2H, J=5 Hz), 3.62 (q, 2H, J=7 Hz), 3.78 (t, 2H, J=5 Hz), 4.10 (s, 2H), 6.4-7.1 (m, 3H), 6.99 (s, 2H).

(iv) 2-[2-(2-ethoxyethylamino)-5-methylbenzylsulfinyl] imidazole 6.00 g (21 mmol) of 2-[2-(2-ethoxyethylamino) 5-methylbenzylthio]imidazole was dissolved in a mixture of 60 ml of dichloromethane, 60 ml of methanol and 6.0 ml of acetic acid. To the resulting mixture were added 9.0 ml of 35 % aqueous hydrogen peroxide and 120 mg of ammonium metavanadate under chilling with ice. The obtained mixture was then stirred for 2.5 hrs. under chilling with ice. After the reaction was completed, 5 % aqueous sodium carbonate was added to the stirred mixture. The organic portion was collected and washed twice with 40 ml of 0.1 N aqueous sodium hydroxide, then subjected to extraction twice with 40 ml of 1 N aqueous sodium hydroxide. The aqueous portion was collected and insolubles were removed by filtration. To the filtrate was little by little added 100 ml of 1 N aqueous ammonium chloride. The deposited crystalline product was collected by filtration and washed with sufficient water. The obtained product was dried under reduced pressure at room temperature to give 3.61 g of the desired compound as a pale brown crystalline powder. (Yield: 57.4 %)

IR $\nu$ (KBr): cm$^{-1}$. 3320, 2960, 2900, 2860, 1615, 1520, 1470, 1435, 1420, 1335, 1310, 1105, 1020, 795, 780.

$^1$H-NMR (CDCl$_3$ / CD$_3$OD = 1/1 v/v): δ. 1.23 (t, 3H, J=7 Hz), 2.13 (s, 3H), 3.24 (t, 2H, J=6 Hz), 3.58 (q, 2H, J=7 Hz), 3.69 (t, 2H, J=6 Hz), 4.29 (d, 1H, J =13 Hz), 4.42 (d, 1H, J =13 Hz), 6.4 7.0 (m, 3H), 7.22 (s, 2H). m.p.: 145–146° C. (decomp.).

EXAMPLE 8

2-[4,6-dimethyl-5-methoxy-2-(2-methoxyethylamino)benzylsulfinyl]imidazole (i)
N-(3,5-dimethyl-4-methoxyphenyl)-2-methoxyacetamide To a solution of 5.00 g (33 mmol) of 3,5-dimethyl-4-methoxyaniline and 7.1 ml of triethylamine in 50 ml of dichloromethane was dropwise added a solution of 4.31 g (40 mmol) of methoxyacetylchloride in 20 ml of dichloromethane under chilling with ice for a period of 30 min. The resulting mixture was stirred for 30 min. at room temperature. The reaction mixture was washed sequentially with 5 aqueous sodium carbonate and 3 N hydrochloric acid, and then dried over anhydrous sodium sulfate. Dichloromethane was distilled off. The residue was crystallized from ether hexane to obtain 6.70 g of the desired compound as a white crystal. (Yield: 90.7 %)

$^1$H-NMR (CDCl$_3$): δ. 2.27 (s, 6H), 3.48 (s, 3H), 3.69 (s, 3H), 3.98 (s, 2H), 7.21 (s, 2H), 8.07 (bs, 1H).

(ii) 3,5-dimethyl-4-methoxy-N-(2-methoxyethyl)aniline

To a suspension of 2.50 g of lithium aluminium hydride in 70 ml of THF was added 6.70 g (30 mmol) of N (3,5- dimethyl-4-methoxyphenyl)-2-methoxyacetamide under chilling with ice for a period of 10 min. The mixture was then heated under reflux for 1 hr. To the resulting mixture, a saturated aqueous sodium sulfate was added under chilling with ice in order to decompose the excess lithium aluminium hydride. The organic portion was collected by decantation and the solvent was distilled off. To the residue were added dichloromethane and water. The dichloromethane portion was collected and dried over anhydrous sodium sulfate. The solvent was distilled off to leave 6.50 g of the desired compound (purity: 96.6 %) as a residual pale yellow oil.(Yield: theoretical)

$^1$H-NMR (CDCl$_3$): δ. 2.22 (s, 6H), 3.22 (t, 2H, J=5 Hz), 3.37 (s, 3H), 3.58 (t, 2H, J=5 Hz), 3.65 (s, 3H), 6.29 (s, 2H)

(iii)
[3,5-dimethy-4-methoxy-N-(2-methoxyethyl)-2-methylthiomethyl]aniline

To a solution of 6.50 g (30 mmol) of 3,5-dimethyl-4-methoxy-N-(2-methoxyethyl)aniline obtained in the above (ii) and 3.3 ml of dimethylsulfide in 100 ml of dichloromethane was added 5.98 g of N-chlorosuccinimide (NSC) under chilling with ice for a period of 30 min. The resulting mixture was stirred for 10 min. under chilling with ice. After the addition of 6.3 ml of triethylamine, the stirred mixture was then heated under reflux for 1 hr. After the reaction was completed, 5 % aqueous sodium carbonate was added. The organic portion was collected and dried over anhydrous sodium sulfate. Dichloromethane was distilled off. The residue was purified by silica gel column chromatography. The solvent was distilled off to obtain 5.62 g of the desired compound as a pale yellow oil. (Yield: 69.6 %)

$^1$H-NMR (CDCl$_3$): δ. 2.06 (s, 3H), 2.25 (s, 3H), 2.27 (s, 3H), 3.27 (t, 2H), 3.40 (s, 3H), 3.63 (s, 3H), 3.65 (t, 2H), 3.75 (s, 2H), 6.37 (s, 1H)

(iv)
[3,5-dimethyl-4-methoxy-N-(2-methoxyethyl)-2-(methylsulfinylmethyl)]aniline 5.62 g (21 mmol) of [3,5-dimethy-4-methoxy-N-(2-methoxyethyl)-2-methylthiomethyl]aniline was dissolved in a mixture of 50 ml of chloroform and 5 ml of methanol. To the resulting solution was added 3.61 g of 85 % m-chloroperbenzoic acid under chilling with ice for a period of 15 min. After the reaction was completed, chloroform and 5 % aqueous sodium carbonate were added. The organic portion was collected and dried over anhydrous sodium sulfate. The chloroform was distilled off. The residue was purified by silica gel column chromatography. The solvent was distilled off to obtain 3.74 g of the desired compound as a pale brown crystal. (Yield: 62.8 %)

$^1$H-NMR (CDCl$_3$): δ. 2.22 (s, 3H), 2.26,(s, 3H) 2.59 (s, 3H), 3.22 (t, J=5 Hz, 2H), 3.39 (s, 3H), 3.61 (t, J =5 Hz, 2H), 3.63 (s, 3H), 3.96 (d, J=14 Hz, 1H), 4.18 (d, J=14 Hz, 1H), 6.43 (s, 1H).

(v)
2-[4,6-dimethyl-5-methoxy-2-(2-methoxyethylamino)-benzylthio]imidazole

Through a solution of 3.74 g (13 mmol) of [3,5-dimethyl-4-methoxy-N-(2-methoxyethyl) -2-(methylsulfinylmethyl)]aniline in 40 ml of dichloromethane was blown gaseous hydrogen chloride for 10 min. at room temperature. The mixture was then stirred for 10 min. After the solvent was distilled off, the residue was dissolved in 20 ml of dichloromethane. The resulting solution was added to a solution of 3.9 g of 2.mercaptoimidazole in 40 ml of ethanol for 10 min., then the solution was stirred for 30 min. at room temperature. Ethanol was distilled off. To the residue were added dichloromethane and 5 % aqueous sodium carbonate. The organic portion was collected and dried over anhydrous sodium sulfate. Dichloromethane was distilled off. The residue was purified by silica gel column chromatography. The solvent was distilled off. The residue was crystallized from ether/hexane to obtain 3.16 g of the desired compound as a white crystalline powder. (Yield: 75.0 %)

$^1$H-NMR (CDCl$_3$): δ. 2.16 (s, 3H), 2.24 (s, 3H) 3.30 (t, 2H, J=5 Hz), 3.42 (s, 3H), 3.60 (s, 3H), 3.67 (t, 2H, J=5 Hz), 4.18 (s, 2H), 6.42 (s, 1H), 7.04 (s, 2H).

(vi) 2-[4,6-dimethyl-5-methoxy-2-(2-methoxyethylamino)-benzylsulfinyl]imidazole 2.00 g (6.2 mmol) of 2-[4,6-dimethyl-5-methoxy-2-(2-methoxyethylamino)benzylthio]imidazole was dissolved in a mixture of 20 ml of chloroform and 2 ml of methanol. To the resulting solution was added 1.27 g of 85 % m-chloroperbenzoic acid under chilling with NaCl-ice for a period of 20 min. After the reaction was completed, chloroform and 5 % aqueous sodium carbonate were added. The organic portion was collected and washed twice with 20 ml of 0.05 N aqueous sodium hydroxide. The resulting mixture was then subject to extraction with 30 ml of 1 N aqueous sodium hydroxide. The aqueous portion was collected and washed with chloroform. To the washed solution was added 45 ml of 1 N aqueous ammonium chloride. The deposited oily product was extracted with dichloromethane. The dichloromethane portion was collected and dried over anhydrous sodium sulfate. Dichloromethane was distilled off and then the residue was crystallized from ether/hexane to give 0.78 g of the desired compound as a pale brown crystalline powder. (Yield: 37 %)

IR ν (KBr): cm$^{-1}$. 3200, 2900, 2880, 1580, 1500, 1460, 1410, 1330, 1240, 1210, 1120, 1090, 1050, 100, 1020, 1000, 860, 750.

$^1$H-NMR (CDCl$_3$ / CD$_3$OD=1/1 v/v): δ. 2.15 (s, 3H), 2.26 (s, 3H), 3.23 (t, 2H, J=5 Hz), 3.42 (s, 3H), 3.63 (s, 3H), 3.67 (t, 2H, J=5 Hz), 4.39 (d, 1H, J =14 Hz), 4.61 (d, 1H, J=14 Hz), 6.46 (s, 1H) 7.27 (s, 2H). m.p.:110–111° C. (decomp.).

PREPARATION EXAMPLE 1

Preparation Example (Tablets)

Each tablet (220 mg) contained the following components:

| Effective component | 50 mg |
|---|---|
| Lactose | 103 |
| Starch | 50 |
| Magnesium stearate | 2 |
| Hydroxypropylcellulose | 15 |

PREPARATION EXAMPLE 2

Preparation Example (Capsules)

Each hard gelatin capsule (350 mg) contained the following components:

| Effective component | 40 mg |
|---|---|
| Lactose | 200 |
| Starch | 70 |
| Polyvinylpyrrolidone | 5 |
| Crystalline cellulose | 35 |

PREPARATION EXAMPLE 3

Preparation Example (Granules)

Each granule (1 g) contained the following components:

| Effective component | 200 mg |
|---|---|
| Lactose | 450 |
| Corn starch | 300 |
| Hydroxypropylcellulose | 50 |

We claim:
1. An imidazole derivative having the formula (I):

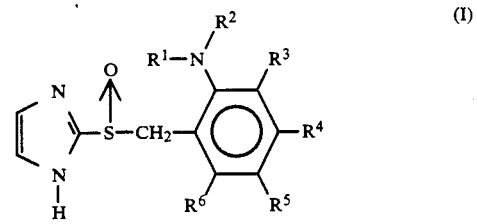

wherein:
R$^1$ is hydrogen or an alkyl group having 1–6 carbon atoms, R$^2$ is an alkyl group having 2–6 carbon atoms of which one hydrogen is substituted with an alkoxy group having 1–4 carbon atoms, each of R$^3$, R$^4$, R$^5$ and R$^6$ independently is hydrogen, a halogen, an alkyl group having 1–6 carbon atoms, an alkoxy group having 1–6 carbon atoms, a fluorine-substituted alkyl group having 1–6 carbon atoms, or a fluorine-substituted alkoxy group having 1–6 carbon atoms.

2. The imidazole derivative as claimed in claim 1, wherein R$^1$ is hydrogen, methyl, ethyl, n-propyl, i-propyl, n-butyl, i-butyl, t-butyl, n pentyl, i-pentyl, neopentyl, n-hexyl or i-hexyl.

3. The imidazole derivative as claimed in claim 1, wherein the alkyl group of R2 is substituted with the alkoxy group at the terminal carbon atom of the alkyl group.

4. The imidazole derivative as claimed in claim 1, wherein said alkoxy group having 1–4 carbon atoms of R$^2$ is methoxy, ethoxy, n-propoxy, i-propoxy, n-butoxy, i-butoxy or t-butoxy, and said alkyl group having 2–6 carbon atoms of R$^2$ is ethyl, n-propyl, i-propyl, n-butyl, i-butyl, t-butyl, n-pentyl, i-pentyl, neopentyl, n-hexyl or i-hexyl.

5. The imidazole derivative as claimed in claim 1, wherein each of R$^3$, R$^4$, R$^5$ and R$^6$ independently is hydrogen, fluorine, chlorine, bromine, iodine, methyl, ethyl, n-propyl, i-propyl, n-butyl, i-butyl, n-pentyl, i-pentyl, neopentyl, n-hexyl, i-hexyl, fluorine-substituted methyl, fluorine-substituted ethyl, fluorine-substituted n-propyl, fluorine-substituted i-propyl, fluorine-substituted n-butyl, fluorine-substituted i-butyl, fluorine-substituted t-butyl fluorine-substituted n-pentyl, fluorine-substituted n-hexyl, fluorine-substituted i-hexyl, methoxy, ethoxy, n-propoxy, i-propoxy, n-butoxy, i-butoxy, t-butoxy, penty-loxy, hexyloxy, fluorine substituted methoxy, fluorine-substituted ethoxy, fluorine-substituted n-propoxy, fluorine substituted i-propoxy, fluorine-substituted n-butoxy, fluorine-substituted pentyloxy or fluorine-substituted hexyloxy.

6. An anti-ulcer composition containing an effective amount of an imidazole derivative having the formula (I):

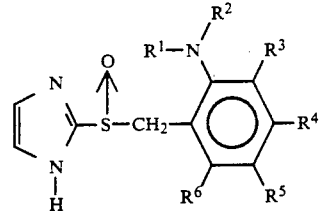

wherein $R^1$ is hydrogen or an alkyl group having 1-6 carbon atoms, $R^2$ is an alkyl group having 2-6 carbon atoms of which one hydrogen is substituted with an alkoxy group having 1-4 carbon atoms, each of $R^3$, $R^4$, $R^5$ and $R^6$ independently is hydrogen, a halogen, an alkyl group having 1-6 carbon atoms, an alkoxy group having 1-6 carbon atoms, a fluorine-substituted alkyl group having 1-6 carbon atoms, or a fluorine-substituted alkoxy group having 1-6 carbon atoms, as an active ingredient and an inert carrier.

* * * * *